United States Patent [19]

O'Connor

[11] Patent Number: 4,758,522
[45] Date of Patent: Jul. 19, 1988

[54] IMMUNOASSAY FOR HUMAN CHROMOGRANIN A

[75] Inventor: Daniel T. O'Connor, San Diego, Calif.

[73] Assignee: The Regents of the University of California, Berkeley, Calif.

[21] Appl. No.: 709,492

[22] Filed: Mar. 8, 1985

[51] Int. Cl.$^4$ .................. G01N 33/566; G01N 33/577
[52] U.S. Cl. .................... 436/501; 436/504; 436/545; 436/548; 436/804; 436/811; 436/815; 435/7; 530/387; 935/104; 935/108; 935/110
[58] Field of Search ............... 436/501, 504, 545, 548, 436/804, 811, 815; 935/104, 108, 110; 530/387; 435/7

[56] References Cited

PUBLICATIONS

Winkler, Scan. J. Immunol., vol. 15, Suppl. 9, 75-96 (1982).
O'Connor et al, J. Clin. Endocrinol. Met., 57(5) 1084-1086 (1983).
Helle et al, Biochim. Biophys. Acta, 533(2) 396-407 (1978).
O'Connor et al, Clin. Res. 30(2) 338A (1982).
Sevier et al, Clin. Chem. 27(11) 1797-1806 (1981).

*Primary Examiner*—Christine M. Nucker
*Attorney, Agent, or Firm*—Brown, Martin, Haller & Meador

[57] ABSTRACT

An immunochemical assay, and compositions used therein, to determine the presence and/or amount of human chromogranin A, which is useful in diagnosis of disease associated with alterations in sympathoadrenal activity.

19 Claims, 3 Drawing Sheets

IMMUNOASSAY FOR HUMAN CHROMOGRANIN A

This invention was made with Government support under Grant No: NHLBI 25457 with the National Institutes of Health and the University of California. The Government has certain rights in this invention.

FIELD OF INVENTION

This invention relates to an immunoassay for monitoring fluctuations in sympathoadrenal activity premised on the detection of human chromogranin A.

BACKGROUND OF THE INVENTION

A variety of physiological events are directly or indirectly under the control of catecholamine hormones secreted by the adrenal glands, or neuronal cells comprising the sympathetic nervous system. The two most widely studied catecholamines are epinephrine and norepinephrine. Epinephrine cause a dramatic elevation in blood pressure arising from arteriolar vasoconstriction, and a concomitant rise in heart rate and cardiac output. Norepinephrine also influences blood pressure, but by a mechanism independent of cardiac output. Rather, norepinephrine increase blood pressure by increasing peripheral vascular resistance.

There is evidence that suggests that abnormally high levels of epinephrine and norepinephrine are responsible for causing hypertension. The latter disease is associated with dysfunction of arterial blood pressure regulation. One means whereby elevated catecholamine levels arise in an organism is their production by tumors, particularly tumors of the adrenals, pheochromocytomas. The latter is of chromaffin tissue origin and, generally, spontaneously secretes catecholamines into the blood.

In addition to their effects on blood pressure, epinephrine and norepinephrine also affect both catabolism and lipid metabolism.

In light of the link between epinephrine and norepinephrine with hypertension and adrenal tumors, it is desirable to have a reliable assay whereby fluctuations in these hormones can be monitored, and hence, utilized in diagnosing the diseases. Several direct tests for detecting catecholamines in physiological fluids are presently in use. These involve chemical analysis, which for the most part is time consuming, insensitive, or unreliable. Indirect tests for catecholamines rely on detecting substances that are secreted along with catecholamines into the blood, and thus their presence can be correlated with circulating catecholamine levels.

Indirect tests for catecholamines are premised on the fact that, prior to being secreted into the blood, catecholamines are stored in vesicles that contain, in addition to catecholamines, a variety of proteins. One such protein, chromogranin A, has been the focus of efforts to establish a reliable indirect assay. While chromogranin A can be satisfactorily assayed in animals other than man, to date attempts at establishing a clinically useful assay for humans have revolved around detecting chromogranin A using microcomplement fixation techniques; and for the most part, these efforts have proved futile.

Considering the role that catecholamines play in the pathogenesis, or symptomatology of particular diseases, it would be of value to have a reliable assay that could be used in a clinical setting to detect the presence of chromogranin A in bodily fluids.

SUMMARY OF THE INVENTION

A method is described for the detection of chromogranin A in humans involving the isolation and labeling of chromogranin A from human cells, followed by utilizing labeled chromogranin A in an immunoassay to detect the presence and/or quantity of chromogranin A in physiological fluids, tissues, or organs. Fluctuations in chromogranin A levels in humans can be related to physiologic, pharmacologic, and pathologic changes in sympathoadrenal activity.

DETAILED DESCRIPTION OF SPECIFIC EMBODIMENTS

Figure 1:
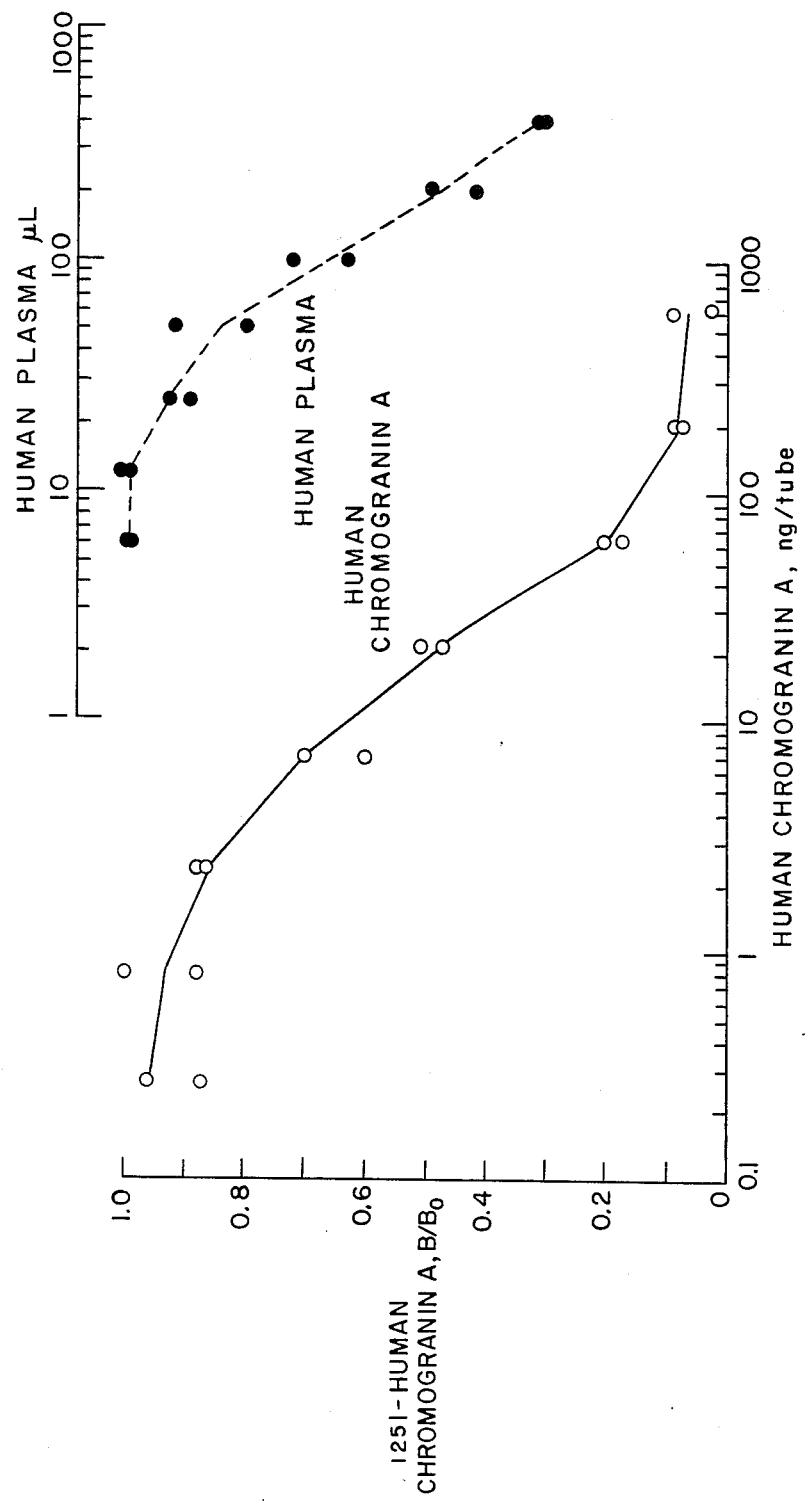

The present invention describes an immunoassay for detecting and/or quantifying human chromogranin A. The method requires successful purification of chromogranin A from human cells, labeling the same with a suitable tracer, and the generation and isolation of antibodies directed against epitopes exhibited by chromogranin A.

1. Isolation and Purification of Chromogranin A.

Chromogranin A is one of several soluble proteins present in secretory vesicles containing catecholamines. Thus, tissue that is exocytotic for catecholamines is a suitable source from which to purify chromogranin A. Human adrenal medullary chromaffin granules, or tumors that originate from chromaffin tissue, are rich in catecholamines and hence particularly useful. Additionally, chromogranin A is present in a variety of tissues other than adrenal tissue, and hence can also be purified from brain, sympathetic neural tissue, or tumors derived therefrom, or other tissues that are highly exocytotic for catecholamine, or a variety of other normal or neoplastic endocrine tissues. Lastly, chromogranin A can be purified from plasma that exhibits a significant circulating level of the protein.

A wide variety of biochemical or immunochemical methods commonly used to purify proteins are available for purifying chromogranin A. One convenient procedure is affinity chromotography wherein antibodies that recognize chromogranin A are covalently attached to a solid support matrix and exposed to an aqueous solution containing chromogranin A under suitable conditions that stimulate chromogranin A binding to antibodies.

Chromogranin A antibody can be bound to a wide variety of solid support materials, but particularly useful are glass beads, agarose and derivatives thereof. Crosslinked derivatives of agarose are commonly employed and can be purchased from Pharmacia Fine Chemicals, Piscataway, New Jersey, under the trade name of Sepharose CL 2B. Sepharose CL 2B is prepared for covalent attachment of chromogranin A antibody as described by J. Porath et al. *Journal of Chromotography* (1973, 86: 53–59). This method involves cyanogen bromide activation of the Sepharose resin, followed by washing and equilibration of the resin with buffer. Chromogranin A antibody is then coupled to the resin by reaction with cyanogen bromide by incubating the resin and antibody for a suitable period of time at 4 degrees centigrade. The resin is then treated with 0.1 molar glycine to block any unreacted active sites on the resin, and washed and stored at 4 degrees centigrade until it is ready to be used.

Chromogranin A is purified using affinity chromotography by applying a sample containing chromogranin A in solution to the resin, which is generally packed in a glass column. After sufficient time has passed to allow chromogranin A to bind to the antibody attached to the resin, the column is washed with a suitable buffer, and then chromogranin A eluted from the column via one of several techniques. Chromogranin A can be eluted by passing chaotropic agents down the column, or exposing the column to high or low pH solutions. Additionally, chromogranin A may be eluted by adjusting the salt concentration of the solution to an empirically determined amount, which dissociates chromogranin A from antibody.

A second procedure for purifying chromogranin A involves purification using a combination of several biochemical procedures. First, chromaffin granules containing catecholamine storage vesicles can be isolated by centrifugation on sucrose density gradients as described by D. O'Connor et al. in *Clinical Experimental Hypertension*, 1982, A4[4&5]: 563–575). Subsequently, the chromaffin granules are exposed to hypotonic buffered phosphate solution (pH 6.5–7.5), and the solution centrifuged at 100,000×g to pellet chromaffin granule membranes. Next, the lysate containing chromogranin A is dialyzed against phosphate buffer to remove catecholamines, and chromatographed as described by D. O'Connor et al. in *Molecular Pharmacology* (1979, 16:529–538) over a concanavalin A-Sepharose column to deplete it of dopamine-beta-hydroxylase. The lysate is concentrated and then subjected to preparative polyacrylamide gel electrophoresis in urea. Chromogranin A is identifiable as a 68,000-dalton, acidic (pH 4.57–4.68), monomeric protein. Areas of the polyacrylamide gels corresponding to chromogranin A are cut out and chromogranin A eluted from the gels either electrically, or by diffusion involving incubating the gels overnight in a solution of phosphate buffer.

Alternatively, the molecule may be puriefied by gel filtration, for example on the resin Sephacryl S-300 (Pharmacia Fine Chemicals, Piscataway, N.J.).

2. Labeling of Chromogranin A

Chromogranin A can be labeled with a wide variety of biochemical labels. Particularly useful in immunoassays are radiotracers, enzymes, free radicals, or fluorescent molecules.

Typical radiotracers used for labeling proteins are $^{125}I$, $^{14}C$, or $^{3}H$. $^{125}I$ is covalently attached to the target molecule by techniques well-known in the art, one being solid phase radio iodination using immobilized lactoperoxidase-glucose oxidase as described by B. Tower et al. in *Life Sciences* (1977, 21:959–966). Labeling with $^{14}C$ or $^{3}H$ necessitates incorporation of $^{14}C$ or $^{3}H$ via labeled amino acids, or sugar precursors by incubating adrenal tissue, or tumor cell lines derived therefrom, with the precursors for sufficient time so that chromogranin A can be synthesized from the labeled precursors.

Representative examples of fluorescent molecules that can be used to label chromogranin A are fluorescein and rhodamine. Additionally, fluorescent molecules that emit detectable electromagnetic radiation may also be employed provided they can be covalently attached to proteins without disrupting their antigenicity.

Lastly, enzymes can be used to label chromogranin A, particularly useful are phosphatases, galactosidases, and dehydrogenases. Generally, enzyme labels are covalently attached to their protein targets by crosslinking reagents, one example being glutaraldehyde. Enzymes bound to their targets are detected by incubation with an appropriate enzyme substrate that yields a measurable color change upon hydrolysis of the substrate. Since immunoassays rely on antibody binding to specific antigenic epitopes, successful use of enzyme labels requires that the antigenicity of the target molecule after attachment of the enzyme be maintained. It is undesirable if the enzyme, because of its size, blocks antibody recognition sites on the protein. Thus, the number of enzyme molecules capable of being bound to chromogranin A is, to a large extent, empirically determined as described by O. Sullivan and Marx in "Methods for the Preparation of Enzyme-Antibody Conjugates for Use in Enzyme Immunoassay" (*Methods of Enzymology*. Eds., J. Langone and H. Binakis. Academic Press, 1981, Vol. 73, Part B:147).

3. Preparation of Chromogranin A Antibodies

Chromogranin A purified as described supra can be used to generate antibodies necessary to perform the immunoassay. Antibodies are obtained by one of two procedures. First, polyclonal antibodies can be produced by conventional methods as described by Vaitukaites in "Production of Antisera with Small Doses of Immunogen: Multiple Intradermal Injections" in *Methods of Enzymology* (Eds. J. Langone and H. Binakis. Academic Press. 1981, Vol. 73, Part B:46); or second, monoclonal antibodies can be generated by either in vivo or in vitro immunization. To obtain polyclonal antibody, an animal is injected one or more injections with antigen, either alone or with an adjuvant, and generally into mice, rabbits, sheep, guinea pigs or other animals capable of yielding an immune response. The immunizations are spaced out over several weeks and the animal is bled and antibody isolated from the serum by techniques well-known to those familiar with the art. Polyclonal antibody contains a mixture of antibodies that recognized several epitopes on the antigen.

The second method of making antibody is to make monoclonal antibody by generating cell lines called hybridomas, each of which secrete a chemically distinct antibody that recognizes a single antigenic epitope. The latter is obtained by the hybridoma technique of H. Kohler and C. Milstein as described in *Nature* (1975, 256:495–496). The procedure consists of one or more immunizations of mice with antigen, either alone or with adjuvant, followed by the removal of the spleen and fusion of splenocytes to a myeloma cell line. The latter is accomplished either chemically with polyethylene glycol, or electrically. Subsequently, the cells are plated in growth media containing drugs that rid the culture of unfused myeloma cells. A fraction of the cells, hybridomas, that grow up produce monoclonal antibodies. Mouse monoclonal antibodies and human monoclonal antibodies can also be produced by in vitro immunization techniques as described by B. Boss in *Brain Research* (1984, 291:193–194) and Bosch and H. Gelfand in *Journal of Immunology* (1977, 118:302–308), respectively.

It is important to note that immunization with intact or naturally occurring chromogranin A may not be necessary to elicit an immune response. It is well-known in the art that peptide fragments obtained from a protein by fragmentation of the protein via proteolysis, sonication, etc., are highly immunogenic. Thus, chromogranin A can be fragmented, peptides isolated and used to produce antibody by in vivo or in vitro immunization. Additionally, to one skilled in the art it is possible to synthesize regions of chromogranin A provided that the DNA coding sequence or amino acid primary structure of chromogranin A are known, and use synthetic peptides to elicit an immune response. It is to be anticipated that since certain amino acids are more immunogenic than others when "seen" by the immune system with neighboring amino acids, that it will be possible to alter the antigenicity of synthetic peptides, perhaps several orders of magnitude relative to their naturally occurring counterparts by synthesizing a peptide composed of such amino acids.

Regardless of whether the antibody is polyclonal or monoclonal, it is often desirable to purify the antibody by standard techniques as described by T. Springer in *Monoclonal Antibodies* (Eds., R. Kennett, T. McKarn, and K. Bechtol. Plenum Press, New York. 1980, 194). Generally, this consists of at least one ammonium sulfate precipitation of the antibody using a 50% ammonium sulfate solution, and subsequent affinity purification by passage over an affinity column containing attached antigen as described by Stryer in *Biochemistry* (Ed., W. Freeman and Co. 1975, 791). The antibody is eluted from the column by several techniques, three being changes in pH, chaotropic agents, or high salt.

4. Performance of the Assay

The assay is premised on competition of labeled chromogranin A with chromogranin A in a sample suspected of containing chromogranin A. While competition between labeled and unlabeled chromogranin A is the principle on which the assay rests, the actual details of performing the assay will be dictated by the nature of the label as well as the type of samples sought to be assayed. A wide variety of biological materials can be assayed for chromogranin A, particularly plasma, serum, urine, cerebrospinal fluid, or saliva. Additionally, tissue or organs suspected of harboring chromogranin A can also be assayed after suitable preparation of the material in order to render chromogranin A accessible to antibody. Methods for extracting chromogranin A from tissues or organs are well-known in the art, and will generally involve disrupting the material in a buffered solution with physical application of force to the tissue, particularly homogenization, or sonication. This process may be aided by the addition of solubilizing detergents. The lysate can, if desired, be clarified of nonsoluble material by a suitable separation step, generally centrifugation, or it can be assayed directly.

The amount of chromogranin A present in biological materials is determined by first demonstrating dose response with known increments of unlabeled chromogranin A so as to construct a standard curve as described R. Yalow and S. Berson in *Hormones* (1964, 4:557–568). The latter relates the amount of labeled molecules present in chromogranin A/chromogranin A-antibody complexes to known amounts of nonlabeled chromogranin A molecules. The procedure can be conducted with chromogranin A, or chromogranin A antibody molecules in solution, or attached to a solid surface. With this information, biological materials with unknown amounts of chromogranin A can be similarly assayed.

The amount of chromogranin A in the assay sample is determined by adding an amount of labeled chromogranin A to a constant amount of chromogranin A antibody or vice versa. The sample sought to be assayed is subsequently added and allowed to compete for antibody binding such that an algebraic relationship exists over a known range of concentrations. Assays utilizing labeled chromogranin A and chromogranin A antibody involve adding chromogranin A to tubes in order that about 30%–60% of the amount added is bound to the antibody.

Conditions for carrying out the assay involve incubating the assay mixture at a temperature of 0–22 degrees centigrade for 1–24 hours at a pH of 7.0–7.4. Next, labeled and nonlabeled chromogranin A bound to chromogranin A antibody is separated from their unbound counterparts. This can be accomplished by a number of techniques as described by R. Yalow and S. Berson, supra, and as described by R. Wide in "Use of Particulate Immunosorbents in Radioimmunoassay" (*Methods of Enzymology*. Eds., J. Langone and H. Binakis. Academic Press, 1981. Vol 73, Part B:203–209). Four satisfactory but not exclusive separation techniques are: precipitation of the chromogranin A/chromogranin A antibody molecule complex with either 50% saturated ammonium sulfate or polyethylene glycol; or, second, precipitation with a second antibody that recognizes the chromogranin A-antibody molecule complex. The third technique removes labeled or nonlabeled chromogranin A that is not bound to the chromogranin A antibody by absorption of the unbound protein to one of several possible absorbents, particularly charcoal, talc, or zirconyl phosphate. Lastly, in those instances where the chromogranin A is affixed to a solid support surface, the site of chromogranin A/antibody binding, unbound reactants can be removed simply by washing the solid support. The means of detecting labeled chromogranin A bound to antibody is dictated by the nature of the label carried by chromogranin A. Generally, this will require radiation measurements with beta or gamma counters if the label is radioactive. Optical density or fluorescent measurements with a spectrometer or fluorometer may be conducted if the label is an enzyme.

The following examples are given to aid in understanding the invention but the invention is not limited to the particular procedures, conditions, or materials described therein.

EXAMPLE 1

Purification of Chromogranin A from Catecholamine Storage Vesicles of Human Pheochromocytoma Cells

A. Tissue Preparation

Approximately 70 grams of human adrenal pheochromocytoma was obtained as a result of surgical removal of the tumor, and immediately placed in ice-cold 0.3M sucrose and transported to the laboratory. Subsequent steps were also conducted at 4 degrees centigrade, unless otherwise specified. Catecholamine storage vesicles were obtained from a purified chromaffin granule subcellular fraction as described by D. O'Connor et al. in *Clinical Experimental Hypertension* (A4[4&5]: 563–575), which is a modification of the sucrose density step gradient method of A. Smith and H. Winkler in *Biochemical Journal* (1967, 103:480–482). The pheochromocytoma tissue is first minced with either scissors or a razor blade, then homogenized in ice-cold 0.3M sucrose, filtered through cheesecloth and then centrifuged at 1000 ×g for ten minutes. The resulting supernatant was decanted and centrifuged at 25,000 ×g for ten minutes, which yields a crude chromaffin granule catecholamine storage vesicle fraction. This fraction is gently resuspended in 0.3M sucrose, and layered onto density step gradients of 1.6M sucrose. The gradients were centrifuged at 10,000 ×g for twelve hours after which time a pink storage vesicle pellet is present in the bottom of the tube.

The catecholamine storage vesicle pellet was resuspended in a hypotonic solution consisting of 0.001M sodium phosphate, pH 6.5, followed by a freeze-thaw cycle in order to lyse the vesicles. The lysate was centrifuged at 100,000 ×g for one hour in an ultracentrifuge to pellet chromaffin granule membranes leaving soluble proteins present in the storage vesicle in the lysate.

Prior to purifying chromogranin A, it is advantageous to remove dopamine-beta-hydroxylase. The latter is accomplished by affinity chromatography of dopamine-beta-hydroxylase to a concanavalin A Sepharose column as described by D. O'Connor et al, in *Molecular Pharmacology* (1979, 16:529–538), and as modified as follows. The catecholamine storage vesicle lysate was dialyzed extensively against 0.01 molar sodium phosphate, pH 6.5, to remove small molecular weight substances, particularly catecholamines. The dialyzed lysate is applied to a concanavalin A-Sepharose column (5×0.9 cm) at a pump rate of 5ml/min. Prior to applying the lysate to the column, the column was equilibrated with 0.01M sodium phosphate buffer, pH 6.5. As a result of this procedure, chromogranin A passes through the column while dopamine-beta-hydroxylase is absorbed.

B. Purification of Chromogranin A by Preparative Polyacrylamide Gel Electrophoresis Elutate from the concanavalin A column was subjected to preparative polyacrylamide gel electrophoresis on a 14×16×0.15 cm polyacrylamide slabs in a Hoefer SE 600 Series slab gel electrophoresis unit (Hoefer Scientific Instruments, San Francisco, Calif.). The unit was cooled to a constant temperature of 15 degrees centigrade by a Lauda K-2/R circulating constant temperature bath (Brinkman Instruments). The polyacrylamide gel matrix was prepared essentially as described by B. Davis in *Annals of Science* (1964, 12:404–427). The gels contained 8M urea included to enhance the separation of chromogranin A from other chromogranins present in the elutate. Generally 2–4 mg of vesicle protein in 1–3 ml of 0.01M sodium phosphate, pH 6.5, was layered onto a pre-electrophoresed running gel, without a stacking gel. Following electrophoresis, the gel's vertical edges were stained with coomassie blue to visualize the chromogranin bands, which were then sliced out of the corresponding nonstained sections of the gel. Next, chromogranin A was eluted overnight from the gel by crushing it into a fine mash and incubated at 4 degrees centigrade with 3–5 ml of 0.1M sodium phosphate (pH 6.3). Finally, the gel fragments were removed the following day by filtration through a 0.8µM microporous membrane filtration unit (Amicon Corporation, Lexington, Mass.) and the chromogranin A is stored at −70 degrees centigrade until used.

EXAMPLE 2.

Preparation of Antibodies to Chromogranin A

Chromogranin A obtained from preparative polyacrylamide gel electrophesis in 8M urea was injected into male New Zealand white rabbits following a modification of the immunization schedule of M. Miras-Portugal and A. Santos Ruiz, *Biochimie* (1977, 59:719–721). Generally, 1 mg of chromogranin A, emulsified in complete Freund's adjuvant, was injected at multiple intradermal sites, on three separate occasions at two-week intervals. One month following the last injection, antisera was collected via central ear artery bleeding.

EXAMPLE 3

Labeling of Chromogranin A—Radioiodination

Purified human chromogranin A was radioiodinated by the solid phase, immobilized lactoperoxidase-glucose oxidase method as described by B. Tower et al. in *Life Sciences* (1977, 21:959–966) and as modified by R. Frigon in *Molecular Pharmacology* (1981, 19:444–450). Generally, it exhibited a specific activity of 250,000 to 300,000 counts/min per ugram of protein and was 70%–90% immunoprecipitable by excess titers of chromogranin A antiserum.

Following radioiodination, the labeled chromogranin A was separated from free iodide and any protein aggregate on a Ultragel ACA-22 gel filtration column (25×1.5 cm) equilibrated with 0.15M NaCl; 0.01M sodium phosphate, pH 7.4; 0.1%, (w/v) ovalbumin; 0.1% (w/v) sodium azide, and eluted at 2 ml/hr, collecting 1-ml fractions. $^{125}$I-chromogranin A was detected by counting 10 µl samples from each fraction for one minute in a gamma counter.

EXAMPLE 4.

Antigenicity of Labeled Chromogranin A and Antibody Titrations

It is desirable to insure that radioiodination of chromogranin A does not adversely affect its antigenicity. Thus, the immunoprecipitability of the radioiodinated chromogranin A was ascertained, along with the titer of rabbit chromogranin A antisera by incubating 6,000 counts/min of $^{125}$I human chromogranin A in 100µl of buffer PBO-10 (0.15M sodium chloride, 1% [w/v]ovalbumin, 0.1% [w/v]sodium azide, and 0.01M sodium phosphate; pH 7.4); 100µl of 0.1 M EDTA, pH 7.4, 0.05% Triton ×100; 100µl of various solutions of chromogranin A antisera also in PBO-10 buffer; and finally, 500 µl of PBO-10. This mixture was allowed to incubate for 24 hours at 4 degrees centigrade, then second antibody and carrier antisera added, which consisted of 100 µl of a 1:8 (v/v) dilution of sheep anti-rabbit gamma-globulin in PBO-10, and 100 µl of 2% (v/v) normal rabbit serum in PBO-10. This mixture was allowed to incubated for another 24 hours at 4 degrees centigrade and the antigen antibody pellet harvested and counted by separating bound and free chromogranin A by centrifugation at 5,000 ×g for twenty minutes at 4 degrees centigrade. The supernatant was aspirated and the antigen-antibody pellet washed with 500 µl of PBO-10 and centrifuged for a second time at 500 ×g for twenty minutes at 4 degrees centigrade. Following aspiration of the supernatant, the antigen-antibody pellet was counted in a gamma counter. The results are graphed as percent of maximum binding at low titer of first antibody, versus the log₁₀ of the first antibody dilution. Based on these results, a suitable titer of chromogranin A antisera was selected to perform the radioimmunoassay.

EXAMPLE 5

Radioimmunoassay

A. Standard Curve Derivation

A working titer of rabbit chromogranin A antisera was chosen to immunoprecipitate 30%–40% of 6,000 counts/min of $^{125}I$ human chromogranin A at 4 degrees centigrade over a 24-hour incubation period in 100 μl of PBO-10 buffer. Following the 24-hour incubation period, a second antibody and carrier antiserum were added consisting of 100 μl of a 1:8 (v/v) dilution of sheep anti-rabbit gamma-globulin in PBO-10 and 100 μl of 2% (v/v) normal rabbit serum in PBO-10. Following a second 24-hour incubation period at 4 degrees centigrade, the antigen-antibody pellet was again harvested and counted as described supra.

The radioimmunoassay standard curve was expressed as counts/min bound (minus blank) in a given tube (B), over counts/min bound (minus blank) at the working titer of first antibody without addition of unlabeled chromogranin A ($B_0$), plotted against log₁₀ of unlabeled chromogranin A added. Typical values for $B_0$ were 1200–1500 counts/min, while typical values for the blank, which consisted of incubation using appropriate solutions of normal rabbit serum instead of chromogranin A antisera, were 140–160 counts/min. All samples were assayed in duplicate at dilutions designed to place pellet counts/min in the 20%–70% $B/B_0$ working range of the standard assay curve.

The assay had a working range of 2 to 60 nanograms per assay tube. Repeated measurements on identical, unknown samples indicated an intra-assay coefficient of variation of 5% (n=10) with an interassay coefficient of variation of 15% (n=5). FIG. 1 shows a standard curve that was generated using the above-described techniques.

B. Assay for Chromogranin A in Biological Fluids

To access the usefulness of the chromogranin A assay, studies were done to measure the presence of chromogranin A as a function of physiologic, pharmacologic, and pathologic changes in sympathoadrenal activity. In a group of eighteen healthy men, the mean plasma immunoreactive level of chromogranin A was 129±12 nanograms per milliliter after twenty minutes of undisturbed recumbancy. Sympathoadrenal function in some of these individuals was altered physiologically or pharmacologically and the effect on plasma chromogranin A levels measured. Plasma chromogranin A increased approximately 66% (P<0.05) upon standing and the rise was complete by fifteen minutes. A further rise in plasma chromogranin A level was not noted despite the individuals being subjected to a dynamic bicycle ergometer exercise in the standing position and a marked rise in heart rate from a basal standing level of 73±5 beats per minute during standing rest, to 125±7 or 156±7 beats per minute during exercise.

Figure 2:
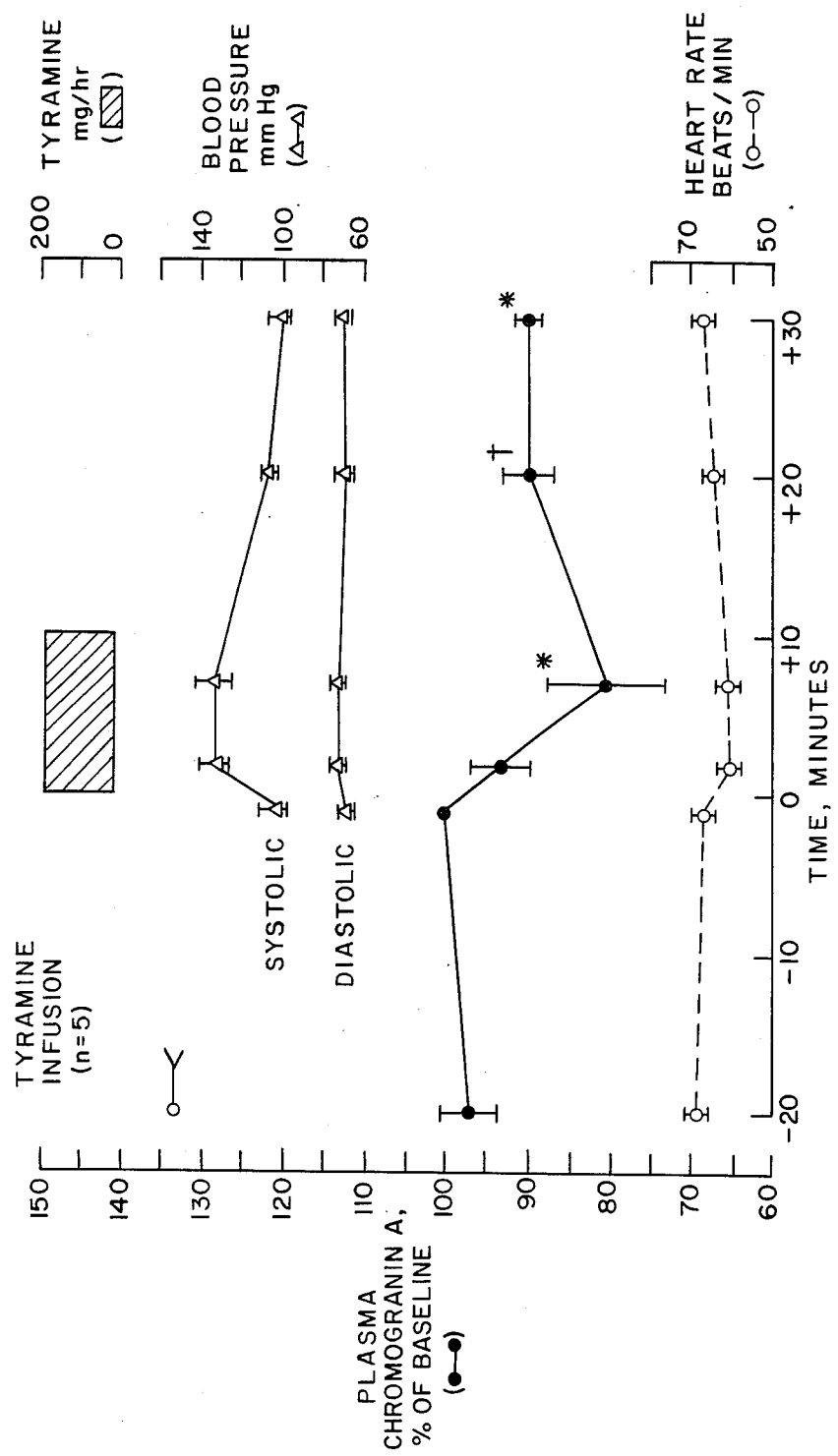

Sympathoadrenal function was altered pharmacologically by inhalation of the vasodilator amyl nitrite by individuals in a supine position. Chromogranin A was observed to increase for a brief period of time (30 seconds) by 7%, in parallel with a transient rise in heart rate. Before inhalation of amyl nitrite the number of beats per minute was 69±6, while after amyl nitrite inhalation it rose to 105±5 beats per minute. After 2 minutes, both plasma chromogranin A and heart rate had returned to normal. Stimulation of nonexocytotic, endogenous catecholamine release by infusion of tyramine as shown in FIG. 2 elevated blood pressure, predominantly systolic pressure, with a modest reflex bradycardia, but caused a fall in plasma chromogranin A by 20%, suggesting a drop in endogenous exocytotic sympathoadrenal tone. Sympathoadrenal deactivation by the ganglionic blocking agent trimethaphan produced a fall in blood pressure and rise in heart rate, with an associated decline in plasma chromogranin A by 8%. On subsequent withdrawal of trimethaphan the ganglionic blockade persisted as shown by a sustained elevation of heart rate over the base line value, and the continued suppression of plasma chromogranin A levels.

Figure 3:
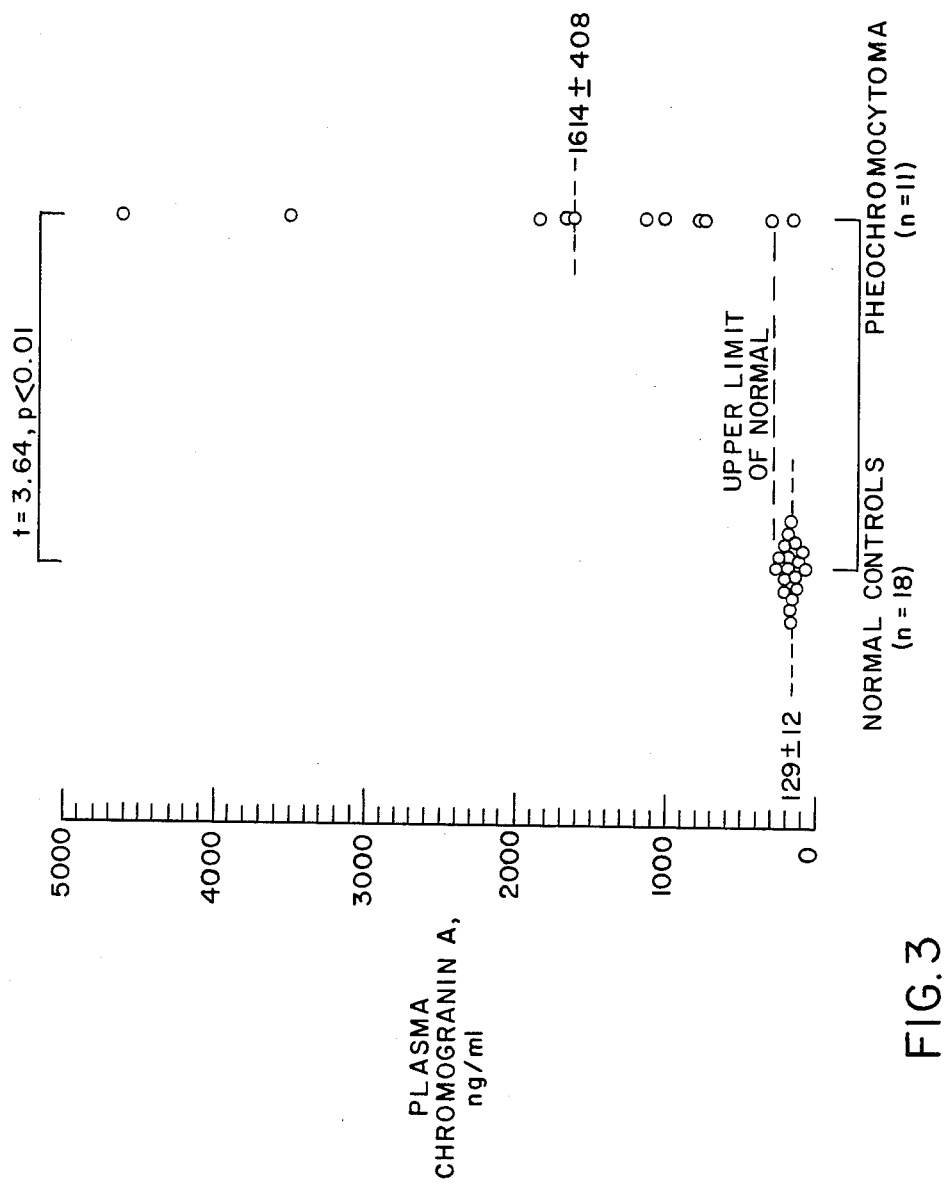

The presence of chromogranin A in eleven patients with pheochromocytoma was determined. As shown in FIG. 3, the plasma chromogranin A levels were markedly elevated when compared with eighteen healthy control individuals. Patients suffering from pheochromocytoma exhibited 1614±408 nanograms per milliliter of chromogranin A compared to 129±12 nanograms per milliliter in the control.

The foregoing invention has been described in some detail to aid in understanding the invention; however, it will be obvious to those skilled in the art that various changes may be practiced that fall within the scope of the claims.

We claim:

1. A method for measuring human chromogranin A comprising:
   combining in an aqueous buffered assay solution a sample suspected of containing said chromogranin A with labeled human chromogranin A, said label providing a detectable signal, and antibodies to human chromogranin A; and
   determining the amount of labeled chromogranin A either bound or unbound to said antibodies to chromogranin A as a measure of human chromogranin A in said sample.

2. A method according to claim 1 wherein said label is radioactive.

3. A method according to claim 2 wherein said radioactive label is $^{125}I$.

4. A method according to claim 1 wherein said sample chromogranin A is obtained from tissue of endocrine or adrenal origin.

5. A method according to claim 4 wherein tissue of adrenal origin is human pheochromocytoma.

6. A method according to claim 1 wherein said sample chromogranin A is obtained from hormone storage vesicles.

7. A method according to claim 4 wherein said sample chromogranin A is obtained by polyacrylamide gel electrophoresis.

8. A method according to claim 6 wherein said sample chromogranin A is obtained from hormone storage vesicles by polyacrylamide gel electrophoresis.

9. A method according to claim 6 wherein said sample chromogranin A is obtained from hormone storage vesicles by chromatography.

10. A method according to claim 1 wherein said antibodies to human chromogranin A are produced by immunication with human chromogranin A.

11. A method according to claim 10 wherein said immunization is in vivo.

12. A method according to claim 11 wherein said in vivo immunization is in mammals.

13. A method according to claim 12 wherein said immunization in vivo in mammals is in sheep or rabbits.

14. A method according to claim 10 wherein said antibodies to chromogranin A are produced by immunization in vitro of human or rodentia lymphoid cells.

15. Polyclonal antibodies to human chromogranin A produced by rabbit or sheep host.

16. Monoclonal antibodies produced by Rodentia or human hybridomas.

17. Labeled human chromogranin A capable of providing a signal in an immunoassay.

18. Labeled human chromogranin A according to claim 17 wherein said label is radioactive.

19. Labeled human chromogranin A according to claim 18 wherein said radioactive substance is $^{125}I$.

* * * * *

UNITED STATES PATENT AND TRADEMARK OFFICE
CERTIFICATE OF CORRECTION

PATENT NO. : 4,758,522

DATED : July 19, 1988

INVENTOR(S) : Daniel T. O'Connor

It is certified that error appears in the above-identified patent and that said Letters Patent is hereby corrected as shown below:

Column 10, claim 10, line 66, "immunication" should instead read --immunization--;

Signed and Sealed this

Twenty-sixth Day of October, 1993

Attest:

BRUCE LEHMAN

Attesting Officer     *Commissioner of Patents and Trademarks*